US005843004A

United States Patent [19]

[11] Patent Number: 5,843,004

Presl et al.

[45] Date of Patent: Dec. 1, 1998

[54] DEVICE FOR THE DIAGNOSIS AND/OR THERAPY OF A PERSON

[75] Inventors: Rudolf Presl, Kreischa, Germany; Walter Bumba, Vienna, Austria

[73] Assignee: Bavaria Patente und Lizenzen Verwertungsgesellschaft mbH

[21] Appl. No.: 601,011

[22] PCT Filed: Aug. 26, 1994

[86] PCT No.: PCT/EP94/02839

§ 371 Date: Jul. 3, 1996

§ 102(e) Date: Jul. 3, 1996

[87] PCT Pub. No.: WO95/05871

PCT Pub. Date: Mar. 2, 1995

[30] Foreign Application Priority Data

Aug. 26, 1993 [AU] Australia ................................ 1717/93

[51] Int. Cl.[6] ........................................................ A61B 5/00

[52] U.S. Cl. ............................................................ 600/595

[58] Field of Search .................................... 600/595, 587; 601/24–26, 49, 90; 482/142

[56] References Cited

U.S. PATENT DOCUMENTS

| | | | |
|---|---|---|---|
| 3,960,144 | 6/1976 | Simjian | 128/58 |
| 4,649,934 | 3/1987 | Fraser et al. | 600/595 |
| 4,650,183 | 3/1987 | McIntyre | 272/96 |
| 4,742,832 | 5/1988 | Kauffmann et al. | 600/587 |
| 4,909,262 | 3/1990 | Halpern et al. | 600/595 |
| 5,020,795 | 6/1991 | Airy et al. | 272/129 |
| 5,060,939 | 10/1991 | Oswald et al. | 272/144 |
| 5,078,152 | 1/1992 | Bord et al. | 600/587 |
| 5,104,364 | 4/1992 | Jones | 482/100 |
| 5,230,672 | 7/1993 | Brown et al. | 482/4 |

FOREIGN PATENT DOCUMENTS

| | | |
|---|---|---|
| 394 806 B | 6/1992 | Austria . |
| 0 166 464 A3 | 1/1986 | European Pat. Off. . |
| 251 656 A2 | 1/1988 | European Pat. Off. . |
| 379 265 A | 7/1990 | European Pat. Off. . |
| 430 067 A1 | 6/1991 | European Pat. Off. . |
| 26 30 299 A1 | 1/1977 | Germany . |
| 42 03 917 A1 | 5/1993 | Germany . |

*Primary Examiner*—Max Hindenburg
*Attorney, Agent, or Firm*—Marshall, O'Toole, Gerstein, Murray & Borun

[57] ABSTRACT

A diagnostic and/or therapeutical device for human beings consists of a stationary frame (5) upon which are mounted an actuating arrangement (3) and a support arrangement (2) so as to rotate around a main axis (4) parallel to the supporting surface (5*a*). The actuating arrangement (3) has at least one actuating element (8) that may be moved by an actuating motor (22) in a predetermined manner with respect to the actuating arrangement (3), as well as means for measuring and displaying or predetermining a resistance offered or to be offered by a person against the movement of the actuating element (8). In order to diversify the possibilities of use of such a device and to allow it to be quickly and accurately adapted to different body sizes, the supporting arrangement (2) is designed as a combined seating and lying frame (10) having a seating plate (11) and a back plate (13) that may be swiveled in relation to the seating plate (11) around an axis parallel to the main axis (4). Adjusting means (26, 27) are provided for moving the seating and lying frame (10) in a vertical plane perpendicular to the main axis (4) in parallel and perpendicular directions (19, 20) in relation to the seating plate (11).

15 Claims, 4 Drawing Sheets

DEVICE FOR THE DIAGNOSIS AND/OR THERAPY OF A PERSON

BACKGROUND OF THE INVENTION

The invention pertains to a device for the diagnosis and/or therapy of a person, consisting of a stationary chassis, on which an actuation arrangement and a support arrangement are seated so as to be pivoted about a main axis parallel to the set-up plane, with the actuation arrangement having at least one actuation element that can be moved by an actuation motor in a predetermined manner relative to the actuation arrangement, as well as a means for measuring and displaying or specifying a resistance exerted or to be exerted by the person against the motion of the actuation element.

A device of the type mentioned above is known from AT-PS 394,806. In this equipment, conceived for use in zero-gravity space, a test subject exerts maximal resistance against the motion of the actuation element. Alongside this measurement, other measurements are performed during the motion, such the measurement of cerebral currents, the measurement of myoelectric currents in the muscles under load and the preparation of an electrocardiogram. It is possible to draw conclusions as to the physical condition of the test subject from these measurements. In that way, changes caused by a relatively long stay in zero-gravity space are to be detected quantitatively. This device, constructed for minimal space requirements, on board a spaceship for instance, naturally does not meet the conditions for routine use under the influence of gravity among persons of differing physical builds, in hospitals, for instance, where the rapid adaptation to every body type and to various physical dimensions is required.

The objective of the invention is to avoid these drawbacks and to refine the known device for terrestrial use, with a great number of possibilities for variation and the ability to adapt rapidly and simply to the person to be examined. According to the invention, this is attained in that the support arrangement is constructed as a combined reclining and sitting chassis, consisting of a seat plate and a back plate that can be pivoted about an axis parallel to the main axis and in that adjustment means are provided for displacing the reclining and sitting chassis in the normal and parallel direction relative to the seat plate in a plane normal to the main axis. The actuation motor here can be constructed as a torque motor and preferably as a pulsed dc motor. Such a motor outputs a preset torque independent of the speed chosen. In particular, such a motor is also capable of yielding this torque even in the stationary state and can thus start up at this torque. This is significant, since the force exerted by the person during the bending or extending is measured by the measurement devices. The reaction of the test subject immediately after beginning the motion or after an inflection point of the bent or extended joint is of particular interest to the physician. It is thus important that precisely this measuring range not be distorted by the startup behavior of the motor. A side effect is that, in this way, isometric measurements, i.e., measurements without macroscopic muscle motion, are possible.

BRIEF SUMMARY OF THE INVENTION

A measurement which is particularly informative to the physician is created if a control arrangement is provided that controls the speed profile of the motor according to a curve specified as a function of the path such that a joint of the test subject, preferably an elbow or a knee joint, is moved at constant angular velocity. In case of linear movement of the hand or foot relative to the shoulder or hip joint, respectively, this means that the velocity of the actuation element must be specified to be proportional to the arc sine of the path traveled. In case of a movement of the actuation element by means of a spindle driven by the motor, this function also applies to the angular velocity of the motor.

In the therapeutic use of the device, for the convalescence of people from injuries, for instance, the resistance to be overcome by the person against the motion of the actuation elements is set in advance. The regeneration of the bodily tissue of a person can be favorably influenced by stepwise elevation of the resistance that is set and is to be overcome within a therapy program.

It is favorable if two actuation elements which can be provided, optionally actuated by the arms or the legs of test subjects, with the two actuation elements each being driven by an actuation motor of its own. In this way, a largely independent measurement is possible for the two arms or legs. Any asymmetric conditions in the test subjects can thus be diagnosed more certainly. It is preferable in this case to provide for the actuation arrangement to consist of two parallel arms, seated so as to rotate about the main axis, and with their inner end faces turned toward one another, and with means for adjusting the axial spacing of the two arms being provided.

In order to achieve a large number of adjustment possibilities, it can furthermore be provided that the twisting of the support arrangement and/or the actuation arrangement about the main axis is done by at least one torsion motor.

In an additional elaboration of the invention it is provided that the means for adjusting the axial spacing of the arms consist at least of an adjustment motor.

A simple and rapid adjustment is achieved by virtue of the fact that the adjustment means for displacing the seat plate of the reclining and sitting chassis contain at least one adjustment motor.

It is also advantageously provided that the back plate has armrests on its two long edges in the vicinity of the arms of a person sitting on the seat plate and projecting in front of said person. It is also possible to provide shoulder supports, preferably adjustable, in the vicinity of the shoulders of a person sitting on the seat plate. In this manner, optimal preconditions are created for the introduction of force by a person onto the actuation elements.

As an additional configuration of the invention, it is advantageous if the seat plate is shaped like a saddle. It can also be provided that a support can be connected to the front of the seat plate and coplanar with it. With a back plate inclined into the plane of the seat plate, a person lying prone on the back plate, seat plate, and support plate can operate the actuation elements by hand, making special arm exercises possible.

It is preferably provided that each actuation element can be linearly displaced in the tangential direction relative to the main axis, whereby a person can exert force on the actuation elements in an ergonomically favorable posture.

In an extremely advantageous embodiment variant it is provided that the force exerted by the person is measured both by means of extensible measuring tapes in the vicinity of the actuation elements and by the power consumption of the actuation motors. This makes a rapid and precise acquisition of data possible. The control of the arrangement is done by a correspondingly trained person by means of the keyboard of the associated control computer.

It is practical for the keyboard to be installed on one side of the reclining and sitting chassis on the stationary chassis.

In this case, the most important parameters for diagnosing performance, such as endurance and strength, are measured. Since measurement data are always person-related, the personal data of the test subject, such as name, gender, height, weight and date of birth, are always recorded when conducting the tests.

By means of the device it is possible to investigate and monitor the effects of physical training on complex functional changes, particularly of the cardiocirculatory system, musculature and fluid balance, under scientific conditions.

After injuries, operations, or medical treatments of elements of the motive arrangement, the corresponding extremities can be both actively and passively trained and measured according to a motion pattern prescribed precisely by the therapist with regard to path, angle and velocity of motion. By having the person in a reclining position it is also possible to eliminate the influence of the person's own weight entirely or in part. By an appropriate, precisely defined increase in the motion parameters, a particularly effective and rapid rehabilitation can be achieved.

Both arms or legs can be moved, either together or individually, cyclically or acyclically.

For reliable use, it is favorable that the actuation motors drive spindles that have a sufficiently high pitch so as not to be self-inhibiting. The invention is described below in greater detail on the basis of an embodiment example illustrated in the figures.

DETAILED DESCRIPTION OF THE INVENTION

Figure 1:
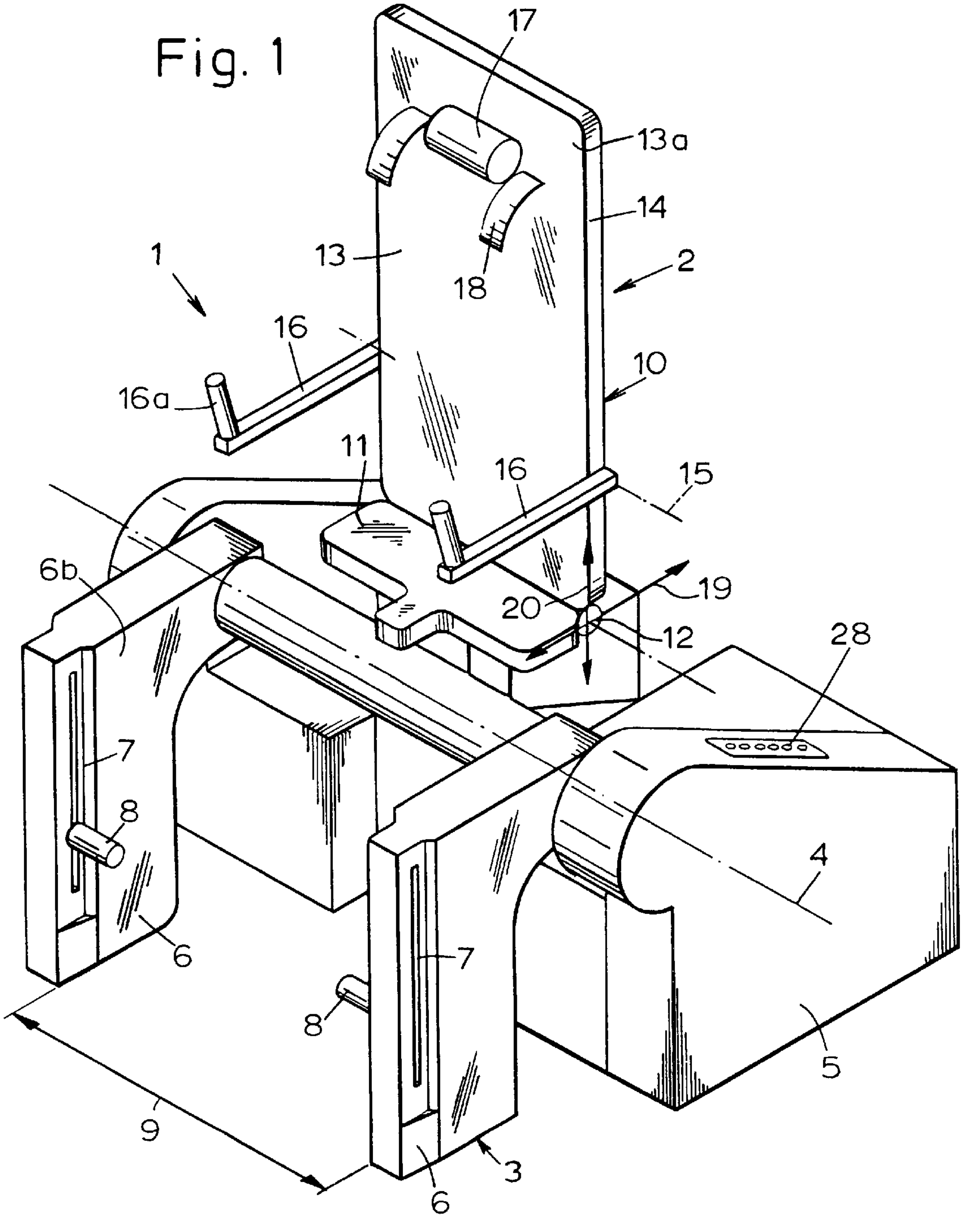
FIG. 1 an axonometric view of the device according to the invention in a possible usage position.

The device 1 consists of the support arrangement 2 and the actuation arrangement 3, which are seated so as to be able to rotate about the main axis 4 on a stationary chassis 5. The actuation arrangement 3 consists of two arms 6 that can be rotated about the main axis 4 and with inner end faces **6*b* facing one another axially, where each arm 6 has guide 7, tangential relative to the main axis 4, for an actuation element 8. The axial spacing 9 of the two arms 8** is adjustable.

The support arrangement 2 consists of a combined reclining and sitting chassis 10, which has a saddle-shaped seat plate 11 and back plate 13 that can be inclined about a pivot axis 12 with respect to the seat plate 11. To the side of the back plate 13 and in the vicinity of its long edges 14, armrests 16, adjustable in height and capable of being pivoted about an axis 15 parallel to the pivot axis 12, are provided. In the end area **13*a* of the back plate 13 opposite the pivot axis, a head and shoulder rest 17 and 18 adjustable in height is installed. The entire reclining and sitting chassis 10 can also be displaced in a plane perpendicular to the main axis 4, both in the direction of the seat plane 19 and also in a direction 20 perpendicular to that, so that the support arrangement 2** can be matched to any possible body size and the respective exercise.

The actuation of the device 1 as well as the adjustment and fitting to various persons is done by the operating personnel by means of a switchboard 29 provided on a stationary chassis.

Figure 2:
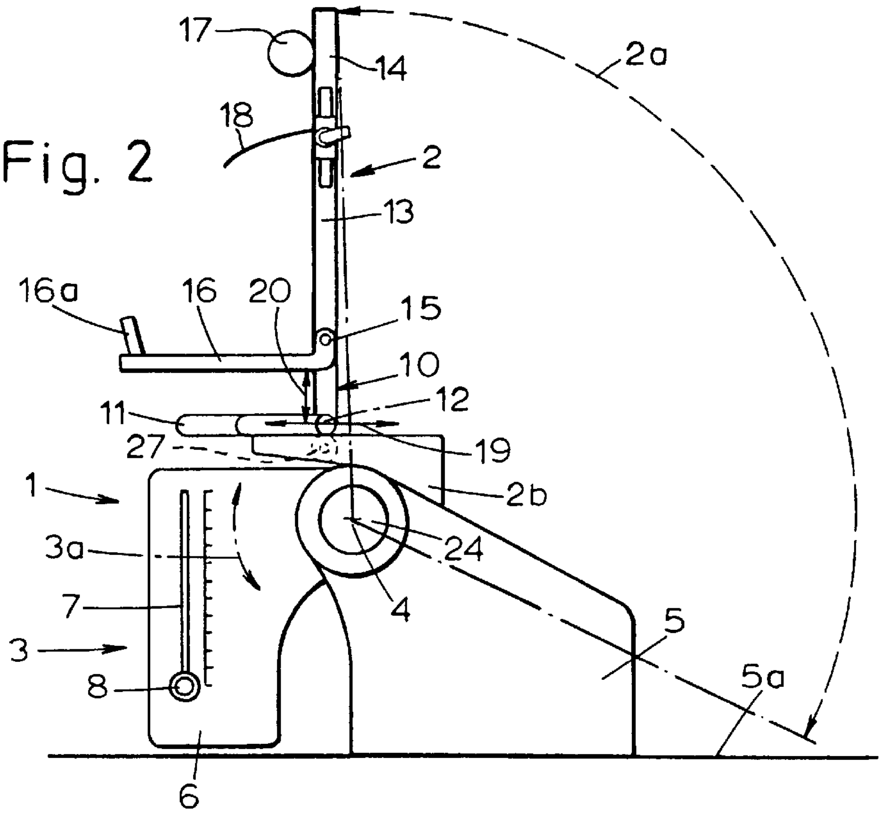
FIG. 2 a side view of the device.
Figure 3:
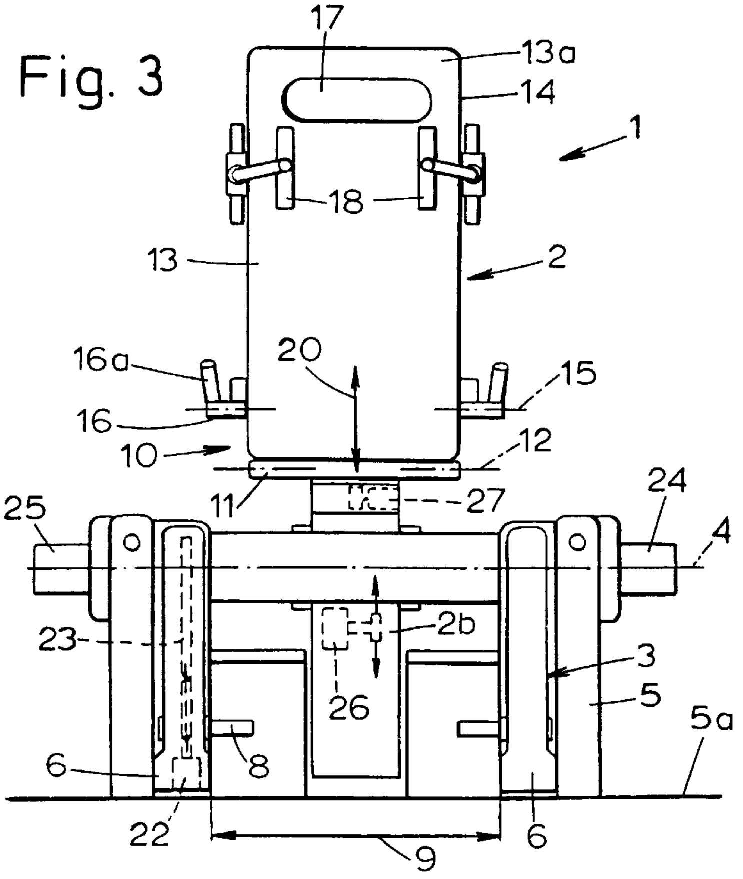
FIG. 3 a front view of the device.

In the usage position of the device 1 shown in FIGS. 1–3, the person to be tested or given therapy sits on the seat plate 11 and supports himself with his back on the back plate 13. The arms lie on the armrests 16, with hands clasping the two grips **16*a*. The height of the seat plate 11 as well as its horizontal position are set such that the person can operate the actuation elements with his feet. The arm, head and shoulder rests 16,17,18 are also fitted to the person. The reclining and sitting chassis 10 can be pivoted together with or independently of the actuation arrangement 3 about the main axis 4 up to about 110°. The person can now take care of leg training by attempting to exert a resistance against the actuation elements 8 moved by motor power. By pivoting the reclining and sitting chassis 10**, the influence of the person's own weight can be partially or completely eliminated. The speed can be set along a freely selectable path as desired.

Figure 4:
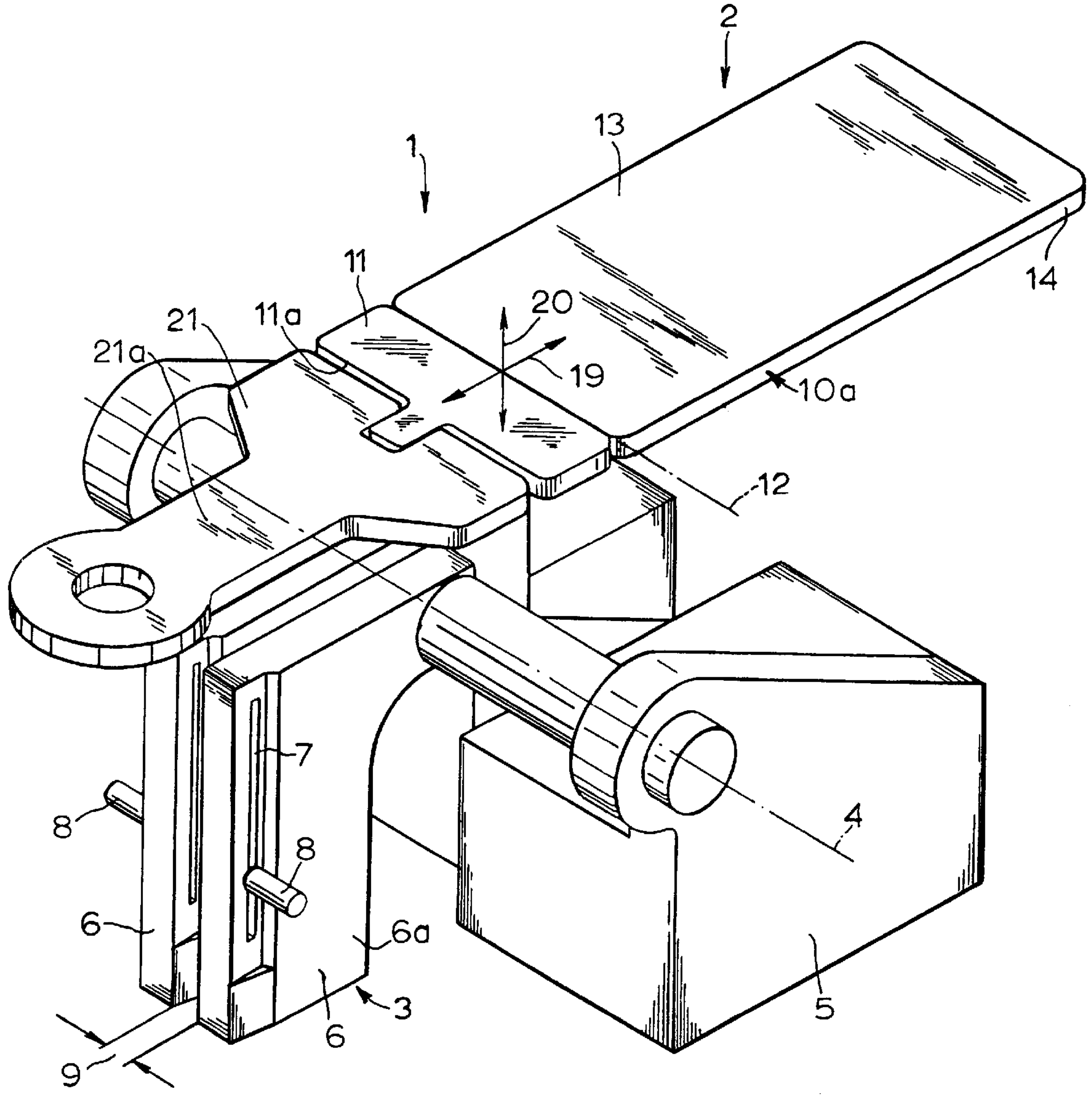
FIG. 4 an axonometric presentation of the device according to the invention in a different usage position.
Figure 5:
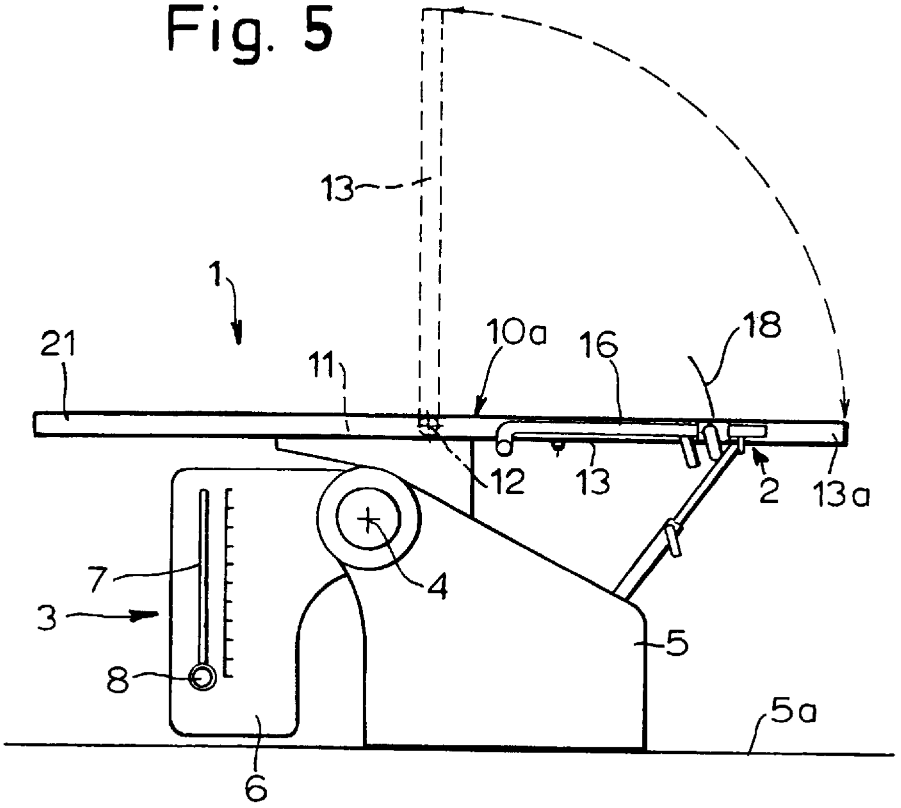
FIG. 5 a side view of the device.
Figure 6:
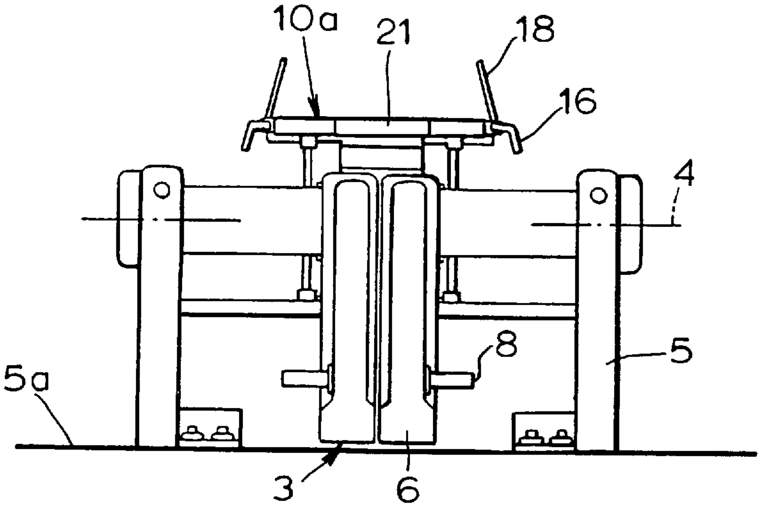
FIG. 6 a front view of the device.

If the person is to perform arm exercises, the usage position of device 1 is set as shown in FIGS. 4–6. In this case the back plate 13 is turned relative to the seat plate 11 about the pivot axis 12 until back plate 11 and seat plate 13 lie in one plane. An additional support plate 21 is coupled in the same plane with the seat plate 11 at the latter's front side **11*a*. The width of the support plate 21 is less in its middle area 21*a* than the width of the seat plate 11. The person assumes a prone position on the reclining chassis 10*a* formed by support plate 21, seat plate 11 and back plate 13 with the person's chest and arm area coming to occupy a position on the support plate 21. The reclining chassis 10*a* is now adjusted in directions 19 and 20 such that the person can actuate the actuation elements 8 with his hands in an ergonomically favorable position. It is practical for the two arms 6 of the actuation arrangement 3 to be moved together axially up to a relatively small spacing 9 resulting from the person's body build. The actuation elements 8 are mounted in this case on the outer surfaces 6*a* of the arms 6. The armrests 16, the shoulder rests 18 and the headrest 17** can be dismounted or swung into a position that does not hinder the person.

In each arm 6, as is visible in FIGS. 2 and 3, an actuation motor 22 is provided which moves the actuation element 8 by means of a spindle 23 along the tangential guide 7. A torsion motor 24 for the pivoting motion **2*a* and 3*a* of the support arrangement 2 or the actuation arrangement 3, respectively, is also provided on the stationary chassis 5. The axial movement of the arms 6 together or apart is produced by the adjustment motor 25 on or in the stationary chassis 5. In order to adjust the seat plate 11 in the direction of the sitting plane 19 or perpendicular to it, additional motors 26 and 27 are housed in a support column which can be pivoted in tandem with the support arrangement 2**.

It is claimed:

1. A device for diagnosis and/or therapy of a person comprising:

a stationary chassis having a main axis;

an actuation arrangement supported on the stationary chassis, the actuation arrangement comprising:

at least one arm the arm, being pivotable about the main axis and adjustable in its position along the main axis;

at least one actuation element associated with the arm;

at least one actuation motor associated with the arm for driving the actuation element; and at least one guide associated with the arm for guiding the actuation element as it is driven by the actuation motor;

means for measuring and displaying or specifying a resistance exerted or to be exerted by the person against the motion of the actuation element;

a support arrangement supported on the stationary chassis, the support arrangement comprising a combined reclining and sitting chassis and being pivotable about the main axis, the combined reclining and sitting chassis having a seat plate and a back plate, the back plate being pivotable relative to the seat plate about an axis at least substantially parallel to the main axis, the seat plate being constructed for alternatively accommodating the buttocks or the upper body of the person and the back plate being constructed for alternatively accommodating the upper body or the buttocks of the person; and means for adjusting the vertical and/or horizontal positioning of the combined reclining and sitting chassis.

2. The device of claim 1 comprising two arms, each constructed in an L-shape and arranged parallel to the other.

3. The device of claim 2 comprising two guides and wherein each L-shaped arm has a short end area and a long end area, the short end area being penetrated by the main axis and one of the guides being arranged on the long end area.

4. The device of claim 1 further comprising a mounting element for mounting the at least one actuation element on the at least one arm, and wherein the at least one actuation motor drives the at least one actuation element via the mounting element.

5. The device of claim 1 comprising four actuation elements and four guides, and wherein each arm has an inner surface and an outer surface, each of the inner and outer surfaces having a guide and an actuation element arranged therein.

6. The device of claim 1 comprising two arms and at least one adjustment motor for adjusting axial spacing of the two arms.

7. The device of claim 1 wherein the at least one guide provides linear guidance of the at least one actuation element in a tangential direction relative to the main axis.

8. The device of claim 1 wherein the forces exerted by the person on the actuation element are measured by extensible measuring tapes in the vicinity of the actuation elements and by the power consumption of the actuation motor.

9. The device of claim 1 wherein the at least one actuation motor drives a spindle having a sufficiently large pitch not to be self-inhibiting.

10. The device of claim 1 further comprising at least one torsion mechanism for pivoting the support arrangement and/or the actuation arrangement about the main axis.

11. The device of claim 1 wherein the adjusting means includes at least one adjustment motor.

12. The device of claim 1 further comprising two arm rests positioned on the back plate to accommodate the arms of the person sitting on the seat plate.

13. The device of claim 1 further comprising an adjustable head and/or shoulder rest positioned on the back plate.

14. The device of claim 1 wherein the seat plate is saddle shaped.

15. The device of claim 1 further comprising a detachable support plate positioned on a front side of the seat plate such that a surface of the support plate adjoins a surface of the seat plate in a flush and coplanar manner.

* * * * *